United States Patent [19]

Raguse et al.

[11] Patent Number: 5,753,093
[45] Date of Patent: May 19, 1998

[54] SENSOR MEMBRANES

[75] Inventors: Burkhard Raguse, Gordon; Bruce A. Cornell, Neutral Bay; Vijoleta L. Braach-Maksvytis, Dulwich Hill; Ronald J. Pace, Farrer, all of Australia

[73] Assignees: Australian Membrane and Biotechnology Research Institute, Homebush; University of Sydney, NSW, both of Australia

[21] Appl. No.: 833,782

[22] Filed: Apr. 9, 1997

Related U.S. Application Data

[62] Division of Ser. No. 406,853, filed as PCT/AU93/00509 Oct. 1, 1993 published as WO94/07593 Apr. 14, 1994, Pat. No. 5,637,201.

[30] Foreign Application Priority Data

Oct. 1, 1992 [AU] Australia .................. PL5069
Jul. 8, 1993 [AU] Australia .................. PL9863

[51] Int. Cl.$^6$ .................................. G01N 27/26
[52] U.S. Cl. .................. 204/418; 204/403; 435/4; 435/7.1; 435/289.1; 435/817
[58] Field of Search ................. 427/331, 337, 427/384, 388.1, 430.1; 204/403, 418, 282, 296; 435/4, 7.1, 11, 289.1, 817

[56] References Cited

U.S. PATENT DOCUMENTS

| 4,661,235 | 4/1987 | Krull et al. | 204/403 |
| 4,849,343 | 7/1989 | Krull et al. | 205/778 |
| 5,401,378 | 3/1995 | King et al. | 204/403 |

*Primary Examiner*—Bruce F. Bell
*Attorney, Agent, or Firm*—Gottlieb, Rackman & Reisman, P.C.

[57] ABSTRACT

The present invention relates to a novel method for producing an electrode membrane combination. This novel method employs compounds including a linker lipid for use in attaching a membrane including a plurality of ionophores to an electrode and providing a space between the membrane and the electrode, the electrode being either in part or totally made up of the linker lipid. The linker lipid comprises within the same molecule a hydrophobic region capable of spanning the membrane, an attachment group used to attach the molecule to an electrode surface, a hydrophilic region intermediate said hydrophobic region and the attachment group and a polar head group region attached to the hydrophobic region at a site remote from the hydrophilic region.

24 Claims, 10 Drawing Sheets

SENSOR MEMBRANES

This is a division of application Ser. No. 08/406,853, filed as PCT/AU93/00509, Oct. 1, 1993, published as WO94/07593, Apr. 14, 1994, now U.S. Pat. No. 5,637,201.

FIELD OF THE INVENTION

The present invention relates to electrode membrane combinations for use in ion selective electrodes and biosensors. In addition, the present invention relates to methods for the production of such electrode membrane combinations and the use of ion selective electrodes and biosensors incorporating such electrode membrane combinations in the detection of analytes. The present invention also relates to novel compounds used in the electrode membrane combinations.

BACKGROUND OF THE INVENTION

Lipid bilayer membranes (also known as black lipid membranes—BLM's) are well known in the biological and chemical fields. The ability of ionophores to modulate the ion flux through these membranes is also well known. Modulation of the ion flux of the membrane in response to specific molecules is also known, especially in the biochemical fields. The lipid bilayer membranes are however extremely fragile and sensitive to non-specific physical and chemical interference. The preparation and properties of the BLM's are fully described in textbooks and literature articles.

It has been known since 1967 that ionophores incorporate into lipid bilayers (P. Mueller et al, Biochem. Biophys. Res Commun., 26 (1967) 298; A. A. Lev et al Tsitologiya, 9 (1967) 102;) in BLM's and that the selective ion flux through the membrane could thus be monitored. Possibility of producing a lipid bilayer containing ionophores on an ionic hydrogel reservoir and using such as an ion selective electrode has also been suggested (U. J. Krull et al, U.S. Pat. No. 4,661,235, Apr. 28, 1987), however no means of obtaining reproducible and stable bilayer membranes have been taught in the art. Using a Langmuir-Blogett bilayer and multilayer approach (T. L. Fare et al Powder Technology, 3, (1991), 51–62; A. Gilardoni et al, Colloids and Surfaces, 68, (1992), 235–242) has been attempted however the ion selectivity was inadequate and the response time was too slow for practical purposes, stability was not adequate and the LB technique is generally considered to be too difficult for industrial applications.

Ionophores in the context of the present invention are any of the naturally occurring lipophilic bilayer membrane compatible ion carriers such as valinomycin, nonactin, methyl monensin or other naturally occurring ion carriers, or synthetic ionophores such as lipophilic coronands, cryptands or podands, or low molecular weight (<5000 g/mol) naturally occurring or synthetic ion channels such as gramicidin, alamethicin, mellitin or their derivatives. Additionally trialkylated amines or carboxylic acids such as phytic acid may serve as proton ionophores.

Ion channels may also include large, lipid membrane compatible, protein ion channels, especially where their function and stability is enhanced through their incorporation into lipid bilayers that are essentially free of extraneous alkane material.

In the broad context of the present invention lipids are deemed to be any amphiphilic molecules, either naturally occurring or synthetic, containing a hydrophobic hydrocarbon group and a hydrophilic head group.

Biosensors and ion selective electrodes incorporating gated ionophores in lipid membrane combinations have been disclosed in International Patent Application Nos PCT/AU88/00273, PCT/AU89/00352, PCT/AU90/00025 and PCT/AU92/00132. The disclosure of each of these references is incorporated herein by reference.

As is disclosed in these applications, suitably modified receptor molecules may be caused to co-disperse with amphiphilic molecules and produce membranes with altered surface binding properties, which are useful in the production of biosensor receptor surfaces of high binding ability and high binding specificities. It is also disclosed that ionophores such as polypeptide ionophores may be co-dispersed with amphiphilic molecules, thereby forming membranes with altered properties in relation to the permeability of ions. There is also disclosure of various methods of gating these ion channels such that in response to the binding of an analyte the conductivity of the membrane is altered. The applications also disclose methods of producing membranes with improved stability and ion flux using chemisorbed arrays of amphiphilic molecules attached to an electrode surface and means of producing lipid membranes incorporating ionophores on said chemisorbed amphiphilic molecules. Additionally, means of co-dispersing ion selective ionophores with amphiphilic molecules thereby producing ion selective membrane combinations are disclosed.

The present inventors have now determined improved means of increasing the stability and ion flux properties of the lipid membranes through the use of novel synthetic lipids and lipid combinations, and novel means of membrane assembly.

In various embodiments the present invention consists in the use of novel bilayer membrane spanning lipids and bilayer lipids and methods of assembly thereof, in order to modulate the properties of the lipid sensor membrane so as to control the ion transport properties of the ionophore, the thickness and fluidity of the membrane, the stability of the membrane, the response to serum, plasma or blood, and the non-specific absorption of proteins to the membrane.

SUMMARY OF THE INVENTION

In a first aspect, the present invention consists in a linker lipid for use in attaching a membrane including a plurality of ionophores to an electrode and providing a space between the membrane and the electrode in which the membrane is either in part or totally made up of the linker lipid, the linker lipid comprising within the same molecule a hydrophobic region capable of spanning the membrane, an attachment group used to attach the molecule to an electrode surface, a hydrophilic region intermediate said hydrophobic region and the attachment group, and a polar head group region attached to the hydrophobic region at a site remote from the hydrophilic region.

In a preferred embodiment of the present invention, the head group region is selected from the group consisting of groups normally associated with naturally occurring or synthetic lipids such as glycerol, phosphatidyl choline, phosphatidyl ethanolamine, mono-, di- or tri-methylated phosphatidyl ethanolamine, phosphatidic acid, phosphatidyl serine, phosphatidyl glycerol, phosphatidyl inositol, disubstituted head groups as found in cardiolipins, ganglioside head groups, sphingomyelin head groups, plasmalogen head groups, glycosyl, galactosyl, digalactosyl, sulfosugar, phosphosugar, N-acetyl neuramic acid, sialic acid, aminosugar head groups, carbohydrate head groups, gal(beta1-3) galNAc(beta1-4) [NAcNeu(alpha2-3]gal(beta1-4)glc-ceramide, oligomers of ethylene glycol, ethylene glycol, oligomers of propylene glycol, propylene glycol, amino acids, oligomers of amino acids, combinations of oligomers of ethylene glycol or propylene glyco functionalised with amino acids or other ionic species or any combination or derivative of the above.

It is generally preferred that the head group is a naturally occurring or synthetic head group that can be used to minimise the non-specific binding of proteins onto the surface of the membrane.

In a further preferred embodiment of the present invention, in order to provide surface characteristics that minimise the non-specific binding of proteins, it is preferred that the head group is a polyethylene glycol ranging in molecular weight of between 600–6000 g/mol.

In a further preferred embodiment, the head group is a phosphatidyl choline group.

In a further preferred embodiment, the head group is a glycerol head group.

In a further preferred embodiment, the head group is a biotin or a biotinylated 6-aminocaproic acid group or an N-biotinylated oligomer of 6-aminocaproic acid.

In a further preferred embodiment, the head group is a Gal(beta1-3)galNAc(beta1-4)[NAcNeu(alpha2-3]gal(beta1-4-Glc-ceramide head group.

In a further preferred embodiment, of the present invention it is preferred that the head group is a group capable of being used to covalently link a protein molecule onto the linker lipid. The protein molecule may be either a receptor such as an antibody or an antibody fragment or may be an enzyme or may be a protein molecule chosen in order to impart biocompatible properties to the membrane.

It is further preferred that the head group is terminated in a carboxylic acid group capable of being used to conjugate the linker lipid with a protein molecule via the amine groups on the protein.

It is further preferred that the head group is a polyethylene glycol in the molecular weight range 400–1000 g/mol terminated in a carboxylic acid group.

In a further preferred embodiment, the head group is a group capable of being covalently linked with a protein molecule via the aldehyde groups generated from the oxidation of carbohydrate groups on the protein molecule.

In a further preferred embodiment, the head group is a hydrazide derivative.

In a further preferred embodiment, the head group is a polyethylene glycol terminated in a carboxy hydrazide derivative.

In a further preferred embodiment, the head group is a group capable of being covalently linked to a protein molecule via free thiol groups on the protein molecule.

It is further preferred that the head group is a maleimide derivative.

In a further preferred embodiment, the head group is a group capable of being covalently coupled to a carboxylic acid group on a protein molecule.

It is preferred that the hydrophobic group has the general structure as shown in FIG. 1 where the group (X) is a hydrocarbon chain that is approximately half the length of the group (Y).

It is preferred that the group (X) will generally be between 10–22 carbons in length and may be a saturated, unsaturated or polyunsaturated hydrocarbon, or may be an alkyl substituted hydrocarbon such as the phytanyl group or other mono- or permethylated hydrocarbon chain.

It is further preferred that the group (X) is a phytanyl group.

In a preferred embodiment of the present invention, the group (Y) in FIG. 1 is a single chain hydrocarbon group of length between 20–60 Å long.

In a further preferred embodiment the group (Y) consists in a single chain group that is between 20–60 Å long and contains within the chain a rigid spacer group such as biphenyl ether or biphenylamine or other biphenyl compound. The rigid spacer group serves the function of making the synthesis of the group simpler as it easily enables the coupling of two smaller alkyl chains onto the rigid spacer group, enabling long sections of the group (Y) to be synthesised readily. The rigid spacer group also enhances the ability of the linker lipid to assume the membrane spanning conformation of the linker lipid as opposed to an U-shaped conformation within the membrane.

In a further preferred embodiment, the group (Y) is a single chain group that is between 30–50 Å long and contains within the chain a N,N'-alkyl substituted 4,4'-biphenyl amine group.

In a further preferred embodiment, the group (Y) is a single chain group that is between 30–50 Å long and contains within the chain a 4,4'-biphenyl ether group.

In a further preferred embodiment, the group (Y) is a bis-hexadecyl 4,4'-biphenyl ether.

In a further preferred embodiment, the group (Y) is a bis-tetradecyl 4,4'-biphenyl ether.

In a further preferred embodiment, the group (Y) is a bis-dodecyl 4,4'-biphenyl ether.

In a further preferred embodiment, the group (Y) is a single chain group that is between 20–60 Å long and contains within the chain an alkyl substituted amine.

In a further preferred embodiment, the group (Y) consist in a single chain group that is between 20–60 Å long and contains within the chain a bis-alkylated pentaerythritol group.

In a further preferred embodiment of the present invention, the membrane spanning lipid is a single chain lipid in which the group (X) in FIG. 1 is absent.

In a further preferred embodiment, the group (Y) contains groups that can alter their conformation in response to an external stimulus such as light, pH, redox chemistry or electric field. The change in conformation within the group (Y) will allow the properties of the membrane such as thickness to be controlled through such external stimulus. This can in turn be used to modulate the conduction of ion channels through modulation of the on/off times of the channels and the diffusion of the channels.

In a preferred embodiment, where the group (Y) alters its conformation in response to light stimulus, the group (Y) contains a 4,4'- or 3,3'-disubstituted azobenzene.

In a further preferred embodiment the group (Y) contains a group that undergoes a spiropyran-merocyanine equilibrium in response to light stimulus.

In a further preferred embodiment of the present invention, the hydrophobic region of the linker lipid consists of oligomers of long chain amino acids, such as 11-aminoundecanoic acid, 16-aminohexadecanoic acid or other amino acid where the carbon chain is preferably between 6–20 carbons long, and where the amino acids are linked via amide linkages.

It is further preferred that the amide groups are tertiary, alkyl substituted amide groups, where the alkyl groups are phytanyl groups or saturated or unsaturated alkyl groups between 1–18 carbons in length.

The nature of the hydrophilic group, the attachment group and the electrode are as described in PCT/AU92/00132.

As is set out in this earlier application it is preferred that the attachment region of the linker lipid is attached to the electrode surface by chemisorption. In a situation where the electrode is formed of a transition metal such as gold, platinum, palladium or silver, it is preferred that the attachment region includes thiol, disulphide, sulphide, thione, xanthate, phosphine or isonitrile groups.

In further preferred embodiment the electrode is formed of gold, silver, platinum or palladium and the attachment region includes either a thiol or a disulfide group, the linker lipid being attached to the electrode by chemisorption.

In an alternate embodiment where the electrode is formed such that a hydroxylated surface is formed on the electrode, it is preferred that the attachment region includes silyl groups such as silyl-alkoxy or silyl chloride groups. The hydroxylated electrode surface may be a prepared by a number of techniques known to someone skilled in the art and may consist of oxidised silicon or oxidised metals such as tin, platinum, iridium.

In yet a further preferred embodiment the electrode is formed of oxidized silicon, tin, platinum or iridium and the attachment region includes silyl groups, the linker lipid being attached to the electrode by covalent attachment.

The hydrophilic region of the linker lipid is preferably a long chain hydrophilic compound. The hydrophilic region of the linker lipid may be composed of oligo/poly ethers, oligo/poly peptides, oligo/poly amides, oligo/poly amines, oligo/poly esters, oligo/poly saccharides, polyols, multiple charged groups (positive and/or negative), electroactive species or combinations thereof. The main requirement of the hydrophilic region of the linker lipid is that it allows the diffusion of ions through the ionophores provided in the membrane. This is achieved by the placement of suitable ion and/or water binding sites along or within the length of the long chain that makes up the reservoir region.

In a preferred embodiment of the invention the hydrophilic region consists of an oligoethylene oxide group. The oligoethylene oxide group may consist of four to twenty ethylene oxide units.

In a further preferred embodiment the hydrophilic region consists of a subunit of tetraethylene glycol attached to succinic acid. This tetraethylene glycol/succinic acid subunit may be repeated 1–4 times.

In a further preferred embodiment the hydrophobic region of a proportion of the linker lipids have covalently attached thereto an ionophore via a hydrophobic spacer.

As set out above the molecule having a hydrophobic region as shown in FIG. 1 incorporating a rigid spacer group provides a number of advantages. This hydrophobic region can, of course, be synthesized separately from the hydrophilic region, attachment region, and polar head group region. This hydrophobic region, or synthetic lipid, is believed to be new in its own right and can be included in bilayer membranes as a membrane spanning lipid to improve various characteristics of the membrane, such as stability.

Accordingly, in a second aspect the present invention consists in a synthetic lipid for use in bilayer membranes, the synthetic lipid having a structure as shown in FIG. 1 in which Y is a single chain group that is between 20 and 60 Å long and contains a rigid spacer group and X are hydrocarbon chains approximately half the length of Y or are absent.

It is preferred that the group (X) will generally be between 10–22 carbons in length and may be a saturated, unsaturated or polyunsaturated hydrocarbon, or may be an alkyl substituted hydrocarbon such as the phytanyl group or other mono- or permethylated hydrocarbon chain.

It is further preferred that the group (X) is a phytanyl group.

In a further preferred embodiment the rigid spacer group is a biphenyl ether or biphenylamine or other biphenyl compound.

In a further preferred embodiment, the group (Y) is a single chain group that is between 30–50 Å long and contains within the chain a N,N'-alkyl substituted 4,4'-biphenyl amine group.

In a further preferred embodiment, the group (Y) is a single chain group that is between 30–50 Å long and contains within the chain a 4,4'-biphenyl ether group.

In a further preferred embodiment, the group (Y) is a bis-hexadecyl 4,4'-biphenyl ether.

In a further preferred embodiment, the group (Y) is a bis-tetradecyl 4,4'-biphenyl ether.

In a further preferred embodiment, the group (Y) is a bis-dodecyl 4,4'-biphenyl ether.

In a further preferred embodiment, the group (Y) is a single chain group that is between 20–60 Å long and contains within the chain an alkyl substituted amine.

In a further preferred embodiment, the group (Y) consist in a single chain group that is between 20–60 Å long and contains within the chain a bis-alkylated pentaerythritol group.

In a further preferred embodiment of the present invention X in FIG. 1 is absent.

In a further preferred embodiment the synthetic lipid includes a head group. Preferred head groups are those listed in the first aspect of the present invention.

The present inventors have determined that the linker lipids described in the first aspect of the present invention as well as the linker molecules described in PCT/AU92/00132, where the attachment group is a thiol and the hydrophobic region is a single hydrocarbon chain, or where the attachment group is a thiol or disulfide group and the hydrophobic region is made up of two hydrocarbon chains, then, when these linker lipids are adsorbed onto a freshly prepared noble metal electrode a close packed monolayer membrane is formed that does not permit the ionophore to easily penetrate into the membrane, hence restricting the ion flux through the membrane. If electrode surfaces are used that are contaminated then the adventitious introduction of defect sites, where the chemisorption of the sulfur containing groups does not occur, will allow ionophores to penetrate into the monolayer. Contamination of the surface of a gold electrode can occur by adsorption of contaminants from air over a period of minutes to hours and results in electrode surfaces that can suffer from poor reproducibility and stability. The present inventors have devised a more controlled method of producing membranes with the required spacing between the linker molecules, while still retaining the efficient and reproducible attachment of the hydrophilic molecules onto the electrode surface during the deposition of the first layer.

In the prior art it has always been believed necessary that on forming a second lipid layer onto coated electrodes an apolar containment vessel is required in order to obtain sealed bilayer membranes on solid substrates. Additionally, the prior art teaches that an alkane co-solvent such as decane, dodecane, tetradecane or hexadecane is beneficial in the formation of highly insulating lipid membranes. The present inventors have now determined means whereby it is possible to form insulating lipid bilayer membranes with a minimal amount or no alkane co-solvent and without the need for an apolar containment vessel. The inventors believe this to be beneficial for control of non-specific serum effects, stability, ion conduction and possibly to reduce non-specific binding of analyte molecules to the containment vessel. Incorporation of ionophores into the bilayer membrane allows the ion flux through the membrane to be modulated depending on the nature of the ionophore as taught in the prior art. Additionally, the present inventors have determined means whereby it is possible to reduce the interference caused by the presence of serum or plasma on the lipid membrane by using lipid combinations that reduce the effect of non-specific ionophore gating effects.

Accordingly, in a third aspect, the present invention consists in a method of producing an electrode membrane combination comprising the steps of:

(1) Forming a solution containing reservoir lipids comprising within the same molecule an attachment region, a hydrophilic region, a hydrophobic regions, and optionally a head group; and spacer compounds comprising within the same molecule a hydrophilic group and an attachment group;

(2) contacting the electrode with the solution from step (1), the composition of the electrode and the attachment regions being selected such that the attachment regions chemisorb to the electrode;

(3) rinsing the electrode;

(4) contacting the coated electrode from step (3) with a solution of lipid and ionophore in a carrier solvent containing less than 2% of an alkane such as decane, dodecane, tetradecane or hexadecane; and (5) adding an aqueous solution to the electrode from step (4).

The hydrophobic region of the reservoir lipid may be either half or full membrane spanning.

In a preferred embodiment, the reservoir lipid is 23-(20'-oxo-19'-oxaeicosa-(Z)-9'-ene)-70-phenyl-20,25,28,42,45-pentaoxo-24aza-19,29,32,35,38,41,46,47,52,55-decaoxa-58,59-dithioahexaconta-(Z)-9-ene as described in PCT/AU92/00132, referred to hereafter as "linker A" or reservoir phytanyl lipid (B) as shown in FIG. 7 or reservoir phytanyl lipid (C) as shown in FIG. 8.

In a preferred embodiment, the spacer molecule is a low molecular weight molecule containing within the same structure a thio or disulfide group and one or more hydroxyl or carboxylic acid groups.

In a preferred embodiment, the spacer molecule is bis(2-hydroxyethyl)disulfide or 2-mercaptoethanol.

In a preferred embodiment, the solution of step 1 contains a mixture of linker A, membrane spanning reservoir lipids and bis-(2-hydroxyethyl)disulfide.

In a preferred embodiment, the solution of step 1 contains a mixture of linker A, membrane spanning reservoir lipids and bis-(2-hydroxyethyl)disulfide in a ratio of 2:1:3.

In a preferred embodiment, the spacer molecule is mercaptoacetic acid, the disulfide of mercapto acetic acid, mercaptopropionic acid or the disulfide of mercaptopropionic acid, 3-mercapto-1,2-propanedio or the disulfide of 3-mercapto-1,2-propanediol.

In a further preferred embodiment the hydrophobic region of a proportion of the reservoir lipids have covalently attached thereto an ionophore via a hydrophobic spacer.

In a preferred embodiment of the present invention, the lipid and ionophore solution contains no alkane such as decane, dodecane, tetradecane or hexadecane.

In a further preferred embodiment the reservoir lipid includes a head group. Preferred head groups are those listed in the first aspect of the present invention.

In a further preferred embodiment of the present invention the lipid in step (4) is glycerol monophytanyl ether.

In a preferred embodiment of the present invention, the lipid is a mixture of glycerol monophytanyl ether and a lipid having a polyethylene glycol group of between 600–6000 g/mol as a head group.

In a further preferred embodiment, the lipid is a mixture of glycerol monophytanyl ether and 1–3% of a lipid having a polyethylene glycol head group. It is further preferred that the polyethylene glycol has a molecular weight in the range of 600–3000 g/mol.

In a further preferred embodiment, the polyethylene glycol containing lipid comprises in the same molecule a phytanyl group attached to a succinate group at one end and a polyethylene glycol 2000 attached to the other end of the succinate.

In a further preferred embodiment, the lipid is a mixture of glycerol monophytanyl ether and a lipid having a phosphatidyl choline head group.

In a further preferred embodiment, the lipid is a mixture of glycerol monophytanyl ether and up to 20% of a lipid having a phosphatidyl choline head group.

In a further preferred embodiment, the lipid is a mixture of glycerol monophytanyl ether and up to 20% of a lipid having a phosphatidyl choline head group and up to 3% of a lipid having as a head group a polyethylene glycol of molecular weight between 600–3000 g/mol.

In a further preferred embodiment, the lipid is a mixture of glycerol monophytanyl ether and a lipid having a head group in which the head group is a Gal(beta1-3)galNAc(beta1-4)[NAcNeu)alpha2-3]gal(beta1-4)Glc-ceramide carbohydrate head group.

In yet a further preferred embodiment a plurality of ionophores are functionalised with a derivative of a low molecular weight analyte whose presence is to be detected.

In this arrangement, the addition of an antibody or other receptor molecule will modulate the ion transport properties of the ionophore. This conductance modulation can then be detected using established impedance spectroscopy or other methods and could also be used to directly monitor the presence of antibodies or other receptors to the low molecular weight analyte. Addition of the test solution to the electrode membrane combination containing the ionophore/antibody or receptor complex will lead to competitive binding of the analyte to the antibody or receptor, thereby allowing the ionophore to again diffuse freely through the membrane. The difference can be determined using techniques such as impedance spectroscopy and can be used to determine the concentration of the analyte in the test solution.

In the alternative arrangement where a synthetic or low molecular weight receptor is attached to the ionophore, the transport properties of the ionophore will be directly modulated on complexation of the analyte of interest by the synthetic or low molecular weight receptor molecule.

In yet a further preferred embodiment of the present invention the ionophore is capable of transporting an ion that is produced by the reaction of an enzyme with its substrate, said enzyme being either covalently or non-covalently attached to the membrane surface.

Addition of a solution containing the substrate will cause the enzyme to produce ionic species which will be transported by the ionophore across the membrane, thus modulating the conductance properties of the membrane, which will be related to the amount of substrate present in solution.

In a preferred embodiment of the present invention, the enzyme is a urease producing ammonium ions from the substrate urea.

In the case where the enzyme is covalently attached to the membrane, it is preferred that the covalent attachment is via a proportion of the lipid molecules that are suitably functionalised for covalent attachment to proteins or by covalent attachment to the head group of the reservoir lipid including a head group.

Although the nature of the carrier solvent does not appear critical it is preferred that the carrier solvent is a solvent or solvent mixture wherein the lipid and ionophore is soluble and which is preferably water soluble. Suitable solvents are common water miscible solvents such as ethanol, dioxane, methanol or mixtures of these solvents. Addition of small amounts of non-water insoluble solvents such as dichloromethane may also be included in the carrier solvent in order to solubilise the lipid and ionophore.

In any of the preferred embodiments of the third aspect of the present invention, the containment vessel may be a containment vessel with polar sides.

It is further preferred that the containment vessel is made of material with a hydrophilic surface.

It is further preferred that the containment vessel is made of a material that minimises non-specific binding of proteins or has its surface modified in order to minimise protein adsorption on addition of the analyte sample to be tested.

In the situation where the reservoir lipid contains within the same molecule a an unsymmetrical disulfide group, where one of the sulfur atoms has a relatively small organic group attached to it, as the attachment region and a single hydrocarbon chain as the hydrophobic group, the cross-sectional area of the disulfide group is larger than that of the single hydrocarbon chain, hence a membrane with close packed hydrocarbon groups does not form on adsorption of the reservoir lipid, thus allowing penetration of ionophores into the adsorbed layer. Accordingly in such a situation it is not essential to use spacer molecules.

As described in the third aspect of the present invention, it is possible to produce membrane layers that are impermeable towards ionophores. The present inventors have determined means whereby it is possible to produce membrane layers by chemisorption of suitable linker lipids, including lipid, membrane spanning and ion channel containing linker molecules, onto an electrode surface such that the conformation of the ion channel and the lipids is controlled. The present inventors have also determined that the presence of the membrane spanning linker lipids enhances the stability of the subsequent lipid bilayer formed, as well as controlling the thickness of the subsequent bilayer membrane. It is known in the art that the lifetime and hence conduction of gramicidin ion channels is controlled in part by the thickness of the bilayer membrane. Thicker bilayer membranes shorten the lifetimes of the ion channel, thinner bilayers increase channel lifetimes. Hence, it is possible to control the lifetime of the ion channel by controlling the thickness of the bilayer through the use of membrane spanning lipids that have different lengths.

The present inventors have also determined that the inclusion of membrane spanning lipid linker lipids that contain polar or bulky head groups decreases the amount of multilayer structure that is obtained in the absence of these lipids.

Furthermore, the inventors have determined that the presence of a molecule having a lipid or hydrophobic component in the solvent is beneficial in enabling the ion channel to assume the proper conformation on adsorption on the electrode surface. Prior art membranes including ion channels are typically formed by doping the formed membrane with ion channels. It is now believed that such a technique results in a number of the ion channels being incorporated into the membrane in states which are non-conducting. Where the channels are helical peptides this may be due to unravelling of the helix, intermeshing of a number of the ion channels to form non-conducting helices, or that the longitudinal axis through the helical peptide is substantially parallel to the plane of the membrane and is thus unable to facilitate the transport of ions across the membrane. The present inventors have developed a method of attaching such ion channels to an electrode such that a higher proportion of the channels exist in a conducting form. The membrane combination thus formed contains a mixture of half-membrane spanning reservoir lipids, membrane spanning reservoir lipids and conducting ion channel linker compounds formed in a close packed layer such that non-linker ion channels do not penetrate into the first layer when the second layer is formed on the coated electrode.

In a fourth aspect the present invention consists in a method of producing an electrode membrane combination, the method comprising the following sequential steps:

(1) Forming a solution comprising ion channels having attached at an end thereof a reservoir region, the reservoir region including a hydrophilic group and an attachment group; and a reservoir lipid, the reservoir lipid comprising a hydrophobic region, a hydrophilic region, an attachment region and optionally a head group in a polar carrier solvent;

(2) Contacting the electrode with the solution from step (1), the composition of the electrode and the attachment groups and the attachment regions being selected such that the attachment groups and the attachment regions chemisorb to the electrode;

(3) After a period of incubation rinsing the coated electrode from step (2) to remove unbound material;

(4) Adding to the rinsed electrode from step (3) a solution comprising ion channels and a lipid in a carrier solvent; and (5) Adding to the electrode from step (4) an aqueous solution such that a lipid bilayer membrane coating the electrode is formed.

In a preferred embodiment of the present invention the ion channels are gramicidin or analogues or derivatives thereof.

In a further preferred embodiment, the gramicidin is a functionalised gramicidin that consists in the same structure of a gramicidin backbone, an hydrophilic group and a disulfide group as shown in FIG. 13 and will be referred to hereafter as "linker gramicidin B".

In a further preferred embodiment the reservoir lipid is reservoir lipid A (23-(20'-Oxo-19'-oxaeicosa-(Z)-9'-ene)-70-phenyl-20,25,28,42,45,-pentaoxo-24-aza-19,29,32,35,38, 41,46,47,52,55-decaoxa-58,59-dithiahexaconta-(Z)-9-ene) or reservoir phytanyl lipid (B) or reservoir phytanyl lipid (C).

The hydrophobic region of the reservoir lipid may be either half or full membrane spanning.

In a further preferred embodiment the reservoir lipid includes a head group. Preferred head groups are those listed in the first aspect of the present invention.

In a further preferred embodiment the reservoir lipid has a biotin containing head group.

In a further preferred embodiment, the reservoir lipid has a head group used to couple the reservoir lipid to a protein molecule or other receptor molecule.

In a further preferred embodiment, the reservoir lipid used in step 1 has a head group used to minimise the non-specific serum interaction on the membrane such as a polyethylene glycol or phosphatidyl choline group.

In a further preferred embodiment, the solution in step 1 further includes a lipid. The lipid in the solutions in step 1 and step 4 may be the same or different.

In a further preferred embodiment, the lipid used in the polar solvent in the solution of step 1 is any natural or synthetic lipid that allows gramicidin to assume the correct conformation for deposition onto the electrode surface in a conducting state, in the lipid solvent mixture used.

In a further preferred embodiment, the lipid in step 1 used in the polar solvent is a glycerol monoalkenoate.

In a further preferred embodiment, the lipid is glycerol monooleate.

In a further preferred embodiment, the polar solvent is ethanol, methanol, trifluoroethanol.

In a further preferred embodiment, the solvent is ethanol or methanol.

It is generally preferred that the electrode from step 2 is treated with an aqueous solution prior to step 3. This is preferably done as soon as possible after contacting the electrode (step 2) with the solution formed in step 1. This, however, is not essential. For example where the polar solvent in step 1 is methanol there is no need to add an aqueous solution to the coated electrode from step 2.

The aqueous solution used in this optional step and in step 5 may be of a large number of solutions such as 0.1 to 1.0M saline.

In a further preferred embodiment, the electrode is treated with a solution prepared in step 1 where the polar solvent is methanol, and where the electrode is rinsed in step with a suitable solvent such as ethanol or methanol.

In a further preferred embodiment of the present invention, the solution in step 1 comprises 140 mM glycerol monooleate, 1 mM reservoir phytanyl lipid (B), and 0.0014 mM linker gramicidin B in ethanol or methanol.

In a further preferred embodiment, the solution in step 1 comprises 140 mM glycerol monooleate, 1.4 mM reservoir phytanyl lipid (B), 0.0014 mM linker gramicidin B, and 0.0014 mM membrane spanning linker lipids in ethanol or methanol.

In a further preferred embodiment, the solution in step 1 comprises 140 mM glycerol monooleate, 14 mM reservoir phytanyl lipid (B), 0.0014 mM linker gramicidin B, and 0.014 mM membrane spanning linker lipids in ethanol or methanol.

In a further preferred embodiment, the linker gramicidin B concentration is varied from 0.000014 mM to 0.014 mM.

In a preferred embodiment the membrane spanning phytanyl lipid (B) concentration is varied from 0.1 mM to 1 mM.

In a preferred embodiment the membrane spanning linker lipid concentration is varied from 0.0001 mM to 1 mM.

In a preferred embodiment of the present invention, the lipid is a glycerol monoalkenoate where the alkenoate group may be an unsaturated hydrocarbon chain of between 16–22 carbons in length.

In a further preferred embodiment, the lipid is a glycerol monoalkyl ether where the alkyl group is a hydrocarbon chain of between 16–22 carbons in length and may contain unsaturation or may be substituted with methyl groups in order to lower its phase transition.

In a preferred embodiment of the present invention, the lipid is glycerol monooleate, glycerol monopalmitoleic, mono-11-eicosenoin, mono-erucin.

In a further preferred embodiment, the lipid is glycerol monooleate or mono-11-eicosenoin.

In a preferred aspect of the present invention, the lipid is glycerol monophytanyl ether.

In a further preferred embodiment of the present invention, the lipid consists in a mixture of glycerol monoalkyl ether or glycerol monoalkenoate and a lipid where the head group consists in a polyethylene glycol group of between 600–6000 g/mol.

In a further preferred embodiment, the lipid is a mixture of glycerol monoalkyl ether or glycerol monoalkenoate and 1–3% of a lipid where the head group is a polyethylene glycol group. It is further preferred that the polyethylene glycol has a molecular weight in the range of 600–3000 g/mol.

In a further preferred embodiment, the polyethylene glycol containing lipid comprises in the same molecule a phytanyl group attached to a succinate group at one end and a polyethylene glycol 2000 attached to the other end of the succinate.

In a further preferred embodiment, the lipid is a mixture of glycerol monoalkyl ether or glycerol monoalkenoate and a lipid where the head group is a phosphatidyl choline head group.

In a further preferred embodiment, the lipid is a mixture of glycerol monoalkyl ether or glycerol monoalkenoate and up to 20% of a lipid where the head group is a phosphatidyl choline head group.

In a further preferred embodiment, the lipid is a mixture of glycerol monoalkyl ether or glycerol monoalkenoate and up to 20% of a lipid where the head group is a phosphatidyl choline head group and up to 3% of a lipid where the head group is a polyethylene glycol of molecular weight between 600–3000 g/mol.

In a further preferred embodiment, the lipid is a mixture of glycerol monoalkyl ether or glycerol monoalkenoate and a lipid where the head group is a gal(beta1-3)galNAc(beta1-4)[AcNeu(alpha2-3)] gal(beta1-4)[AcNeu(alpha2-3)] carbohydrate head group (Gal$\beta$1-3-GalNAc$\beta$1-4Gal(3-2$\alpha$-NeuAc)$\beta$1-4Glc-1-1 ceramide head group).

Although the nature of the carrier solvent does not appear critical, it is preferred that the carrier solvent is a solvent or solvent mixture wherein the lipid and ionophore is soluble and which is preferably water soluble. Suitable solvents are common water miscible solvents such as ethanol, dioxane, methanol or mixtures of these solvents. Addition of small amounts of non-water insoluble solvents such as dichloromethane may also be included in the carrier solvent in order to solubilise the lipid and ionophore.

In any of the preferred embodiments of the fourth aspect of the present invention, the containment vessel may be a containment vessel with polar sides.

It is further preferred that the containment vessel is made of a material with a hydrophilic surface.

It is further preferred that the containment vessel is made of a material that minimises non-specific binding of proteins or has its surface modified in order to minimise protein adsorption on addition of the analyte sample to be tested.

In yet a further preferred embodiment of this aspect of the present invention the solutions in steps (1) and (4) contain less than 2%, and preferably 0% of an alkane such as decane, dodecane, tertradecane or hexadecane.

Without wishing to be bound by scientific theory it is believed that the method of the present invention provide a greater proportion of conducting ion channels due to the fact that the ion channels in step 1 are able to assume their native configuration in the lipid component of the reservoir lipid. These ion channels are then laid down and attached to the electrode via the attached reservoir regions in this conformation. The rinsing of the membrane to remove the unbound reservoir lipid then removes all unbound ion channels. This should result in the majority of the bound ion channels being in a conductive configuration. The subsequent addition of a lipid results in the formation of a lipid bilayer with the bound ion channels present in the lower layer. The ion channels added in step 4 will then partition primarily in the upper layer.

Another advantage provided by the method of this aspect of the present invention is that it enables accurate adjustment of the proportion of ion channels in the upper layer of the membrane bilayer.

The present inventors have determined a method of applying a hydrogel protective layer onto a membrane biosensor in order to increase the stability of the membrane and in order to protect the membrane biosensor from interferents such as those present in blood.

Referring to the hydrogels, suitable polymers may either be regular homopolymers containing substantially no other material in their matrices, slightly crosslinked homopolymers, or they may be copolymers prepared from two or more monomers.

Accordingly, in a fifth aspect the present invention consists in a biosensor for use in detecting the presence or absence of an analyte in a sample, the biosensor comprising an electrode and a bilayer membrane comprising a top layer and a bottom layer, the bottom layer being proximal to and connected to the electrode such that a space exists between the membrane and the electrode, the conductance of the membrane being dependent on the presence or absence of the analyte, the membrane comprising a closely packed array of amphiphilic molecules and a plurality of ionophores dispersed therein, and a layer of a hydrogel formed on top of the lipid bilayer membrane, the hydrogel allowing the passage of the analyte molecule to be detected.

In a preferred form of the present invention, the hydrogel consists in a thermosetting gel that is deposited onto the preformed lipid bilayer membrane at a temperature where the thermosetting gel is in the fluid phase and subsequently gels as the temperature is lowered below the gels setting temperature, thus forming the protective gel membrane above the lipid bilayer membrane.

In a further preferred embodiment of the present invention, the thermosetting gel is an agar gel.

In a further preferred embodiment, the gel contains between 0.3–5% agar.

In a further preferred embodiment, the thermosetting gel is a gelatine gel.

In a further preferred embodiment of the present invention, the hydrogel consists in an in situ polymerised hydrogel, where a solution of gel forming monomer is added to a preformed lipid bilayer membrane and is subsequently polymerised such that an hydrogel is formed as the protective gel membrane above the lipid bilayer membrane.

In a further preferred embodiment, the gel forming monomer is an acrylic acid or an acrylic acid derivative that is polymerised by free radial polymerisation.

In a further preferred embodiment, the hydrogel may be formed from hydroxyalkyl acrylates and hydroxyalkyl methacrylates, for example, hydroxyethyl acrylate, hydroxypropyl acrylate and hydroxybutylmethacrylate; epoxy acrylates and epoxy methacrylates, such as, for example, glycidyl methacrylate; amino alkyl acrylates and amino alkyl methacrylates; N-vinyl compounds, such as, for example, N-vinyl pyrrolidone; amino styrenes; polyvinyl alcohols and polyvinyl amines.

In a further preferred embodiment, the gel forming monomers consist of acrylamide and a bisacrylamide cross-linker.

In a further preferred embodiment, the hydrogel is formed from cross-linked hydroxyethyl acrylate or hydroxyethyl methacrylate or other biocompatible gel.

In a further preferred embodiment of the present invention, the hydrogel incorporates a number of groups that alter the partition of interferents and/or analyte molecules into the gel layer by means of altering the net charge of the hydrogel.

In a further preferred embodiment, the hydrogels contain enzymes such as urease that convert a substrate into an ionic species that is able to be detected by the lipid bilayer membrane sensor. In the case of the enzyme urease, urea would be converted to ammonium ions which could be detected by a lipid bilayer sensing membrane incorporating an ammonium selective ionophore.

In an sixth aspect, the present invention consists in an electrode membrane combination comprising an electrode and an ionically insulating monolayer membrane, the membrane comprising a closely packed array of amphiphilic molecules and a plurality of ionophores dispersed therein, said amphiphilic molecules comprising within the same molecule a hydrophobic region, an attachment region attached to the electrode, a hydrophilic region intermediate said hydrophobic and attachment regions, the space formed by said hydrophilic region between the electrode and the membrane being sufficient to allow the flux of ions through the ionophores, and a head group attached to the hydrophobic portion of the molecule at a site remote from the hydrophilic region.

In a preferred embodiment of this aspect of the present invention, the monolayer membrane molecule has a hydrophobic region that consists of oligomers of long chain amino acids, where the amino acids are linked via amide linkages, that are substituted at the nitrogen with hydrocarbon alkane groups. It is preferred that the structure of the amino acids is such that the amino group is typically separated from the acid group by an alkane chain of between 6–20 carbons long, and that the alkane chains attached to the nitrogen are typically between 10–20 carbon atoms long and may be either saturated or contain unsaturated groups. Additionally, the alkane groups may consist of phytanyl or similar substituted alkane groups.

In a further preferred embodiment, the membrane consists in a monolayer membrane molecule where the hydrophobic region consists in a tertiary, trialkyl amine that is functionalised at two of the alkyl chains such that the tertiary amine is attached to a monoalkylsubstituted glycerol, monoalkyl substituted glutamic acid or other commonly used groups normally used in lipid synthesis in order to form dialkyl lipids. The unfunctionalised alkyl group attached to the amino group may consists of an hydrocarbon chain, typically of carbon chain length 1 to 20 carbons long and may be unsaturated or additional alkyl substituted. The two functionalised alkyl chains attached to the amino group are typically 10 to 20 carbon atoms long. The monoalkyl substituents of the monoalkyl substituted glycerol, glutamic acid or other commonly used group would typically be a hydrocarbon chain that is the same length as the functionalised alkyl chain attached to the amine group.

In a further preferred embodiment, the membrane consists in a monolayer membrane where the hydrophobic region consists in a tetra alkylated pentaerythritol derivative where two of the alkyl chains are functionalised so as to allow attachment to monoalkyl substituted glycerol, glutamic acid or other commonly used groups normally used in lipid synthesis. The unfunctionalised and functionalised alkyl groups may be the same as described above.

The head groups attached to the hydrophobic region of the membrane may comprise of any of the hydrophilic head groups as described in the first aspect of the present invention. Similarly, the attachment region and hydrophilic ionic reservoir region are any of the groups described in PCT/AU92/00132.

In yet a further preferred embodiment of the present invention the ionophore is capable of transporting an ion that is produced by the reaction of an enzyme with its substrate, said enzyme being either covalently or non-covalently attached to the membrane surface.

Addition of a solution containing the substrate will cause the enzyme to produce ionic species which will be transported by the ionophore across the membrane, thus modulating the conductance properties of the membrane, which will be related to the amount of substrate present in solution.

In a preferred embodiment of the present invention, the enzyme is a urease producing ammonium ions from the substrate urea.

In the case where the enzyme is covalently attached to the membrane, it is preferred that the covalent attachment is via a proportion of the lipid molecules that are suitably functionalised for covalent attachment to proteins.

DETAILED DESCRIPTION OF THE INVENTION

In order that the nature of the present invention may be more clearly understood preferred forms thereof will now be described with reference to the following examples.

EXAMPLE 1

Figure 2:
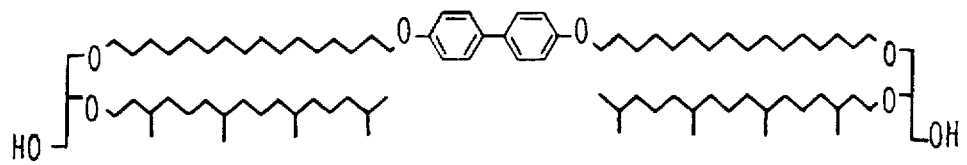
FIG. 2 is a structural diagram of a diol resulting from the debenzylation of a bis-benzyl protected membrane spanning lipid.
Figure 4:
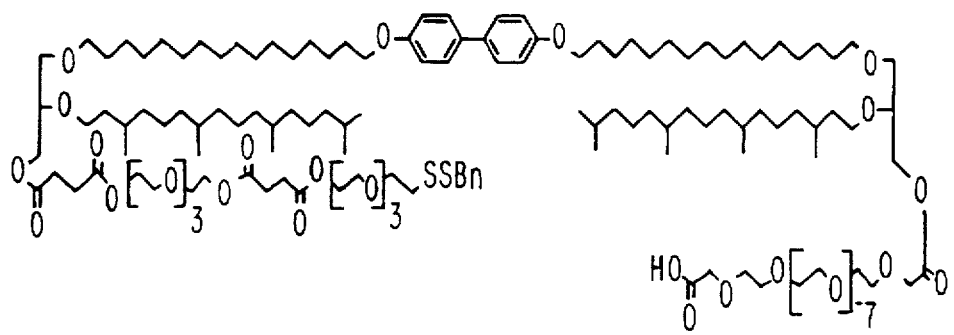
FIG. 4 is a structural diagram of a membrane spanning lipid containing a dicarboxy polyethylene glycol 400 head group.
Figure 5:
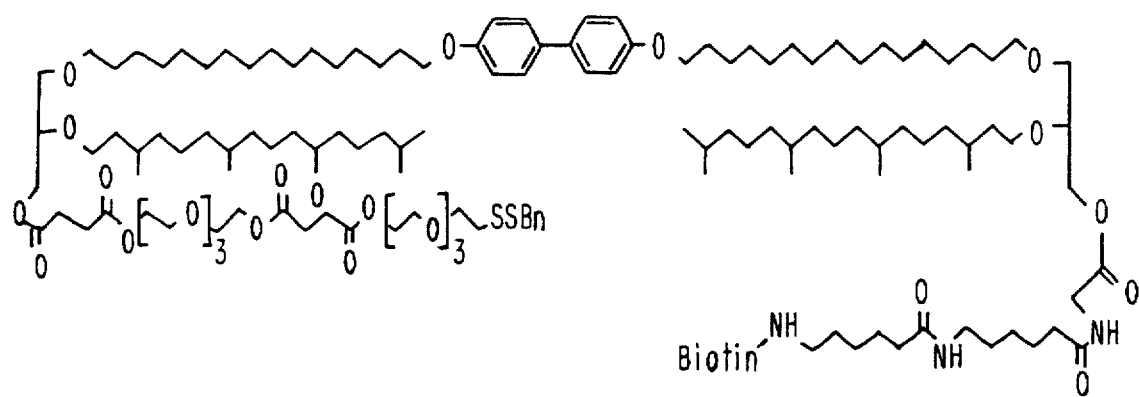
FIG. 5 is a structural diagram of a further membrane spanning lipid of the present invention.

Synthesis of membrane spanning lipids 1,3-Benzylidine glycerol was prepared according to the method of H. S. Hill et al in Carbohydrates and Polysaccharides, 50, (1928), 2242–2244. The 1,3-benzylidine glycerol was then treated with sodium hydride in tetrahydrofuran and phytanyl bromide under reflux for 24 hours to give the glycerol 2-phytanylether 1,3-benzylidine. This ether was then treated with a mixture of potassium borohydride and boron trifluoride etherate in refluxing tetrahydrofuran for 24 hours to give the glycerol 1-benzylether 2-phytanylether. The product was then treated with sodium hydride and 1,16-dibromohexadecane in refluxing tetrahydrofuran for 24 hours to yield the glycerol 1-benzylether 2-phytanylether 3-(16-bromohexadecyl) ether. The homologous compounds using 1,12-dibromododecane, or 1,14-dibromotetradecane were produced in similar fashion. Treatment of the product with biphenol and sodium hydride in refluxing tetrahydrofuran gave the bis-benzyl protected membrane spanning lipid which, after isolation, was debenzylation using palladium on charcoal to give the diol shown in FIG. 2. Addition of a reservoir component as described in PCT/AU92/00132 in the presence of dicyclohexylcarbodiimide and dimethylamino pyridine gave the membrane spanning lipid shown in FIG. 3 which contains an alcohol head group (MSL-OH). Treatment of this membrane spanning lipid with the diacidchloride of an acid functionalised polyethylene glycol 400 (average molecular weight 400 g/mol) followed by an aqueous workup gave the membrane spanning lipid shown in FIG. 4 (MSLPEG400COOH) which contains a dicarboxy polyethylene glycol 400 head group. Treatment of the diol shown in FIG. 2 with firstly, one equivalent of BOC-glycine/dicyclohexylcarbodiimide and dimethylamino pyridine and isolation of the monosubstituted compound, secondly with trifluoroacetic acid to remove the BOC group, thirdly treatment with a biotin-xx-N-hydroxysuccinimide (where the X group is an 6-aminocaproic acid group), and fourthly, treatment of the product with the reservoir component as above in the presence of dicyclohexylcarbodiimide and dimethylamino pyridine gave the membrane spanning lipid as shown in FIG. 5 (MSLXXB).

EXAMPLE 2

Effect of Small Spacer Compound on Conduction through the First Layer

A freshly prepared evaporated 2 mm$^2$ gold on glass electrode was immersed in a solution of linker (a) and bis(2-hydroxyethyl)disulfide (HEDS) at various ratios (final concentration was 0.2 mM in ethanol), within five minutes of preparation. After allowing the disulfide species to adsorb for a period of between 30 minutes to 3 days the electrodes were rinsed with ethanol, dried and clamped in a containment vessel. Two microlitres of an ethanol solution of glycerol monooleate (GMO) (140 mM) and valinomycin (GMO/valinomycin ratio 3000:1) with 8% tetradecane (v/v) was added to the electrode. The electrode was then rinsed twice with 0.5 ml of 0.1M saline solution. After the impedance spectrum was obtained, the sodium chloride solution was exchanged with 0.1M potassium chloride solution. The absolute impedance values at 1 Hz are shown in Table 1 below.

TABLE 1

| Ratio Linker (A):HEDS | NaCl(0.1M) | KCl(0.1M) log/Z/ at 1Hz |
|---|---|---|
| 1:0 | 7.62 | 7.40 |
| 20:1 | 7.50 | 7.25 |
| 5:1 | 7.85 | 6.81 |
| 1:1 | 7.62 | 6.61 |
| 1:2 | 7.81 | 6.35 |
| 1:20 | 7.54 | 6.38 |

As can be clearly seen, the conduction of the potassium via the valinomycin increases as the linker (A) molecule is spaced further apart by the HEDS molecule.

Figure 3:
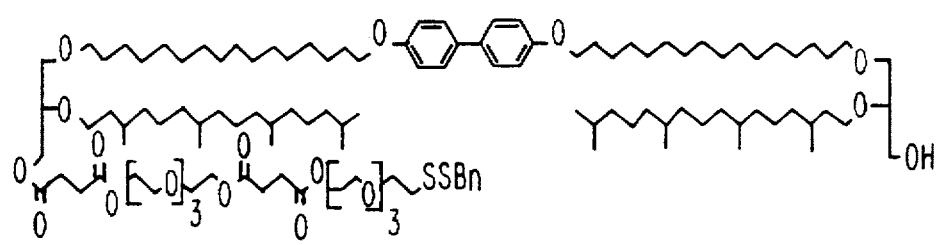
FIG. 3 is a structural diagram of a membrane spanning lipid containing an alcohol head group.

When the above experiment is repeated using the membrane spanning lipid shown in FIG. 3 (MSL-OH) with various HEDS ratios similar results were obtained as shown in Table 2. At high MSL-OH ratios the lipid membrane systems appear to contain multilammellar structures, hence the overall high impedance

TABLE 2

| Ratio MSL-OH:HEDS | NaCl(0.1M) | KCl(0.1M) log/Z/ at 1Hz |
|---|---|---|
| 1:0 | 7.8 | 7.3 |
| 1:10 | 7.5 | 6.4 |
| 1:100 | 7.0 | 6.1 |
| 0:1 | 6.9 | 6.1 |

Adsorpotion of a monolayer of MSLPEG400COOH onto a 2 mm$^2$ gold electrode with no HEDS, followed by the addition of GMO/tetradecane as described above, resulted in a bilayer membrane with an impedance of 200 kohms at 100 Hz. Conversely, an electrode with a MSLOH first layer followed by the addition of GMO/tetradecane as described above resulted in a membrane containing thicker or multilamellar structures as seen by the high impedance of 650 kohms at 100 Hz.

EXAMPLE 3

Formation of a lipid bilayer membrane without a sealing alkane

Figure 6:
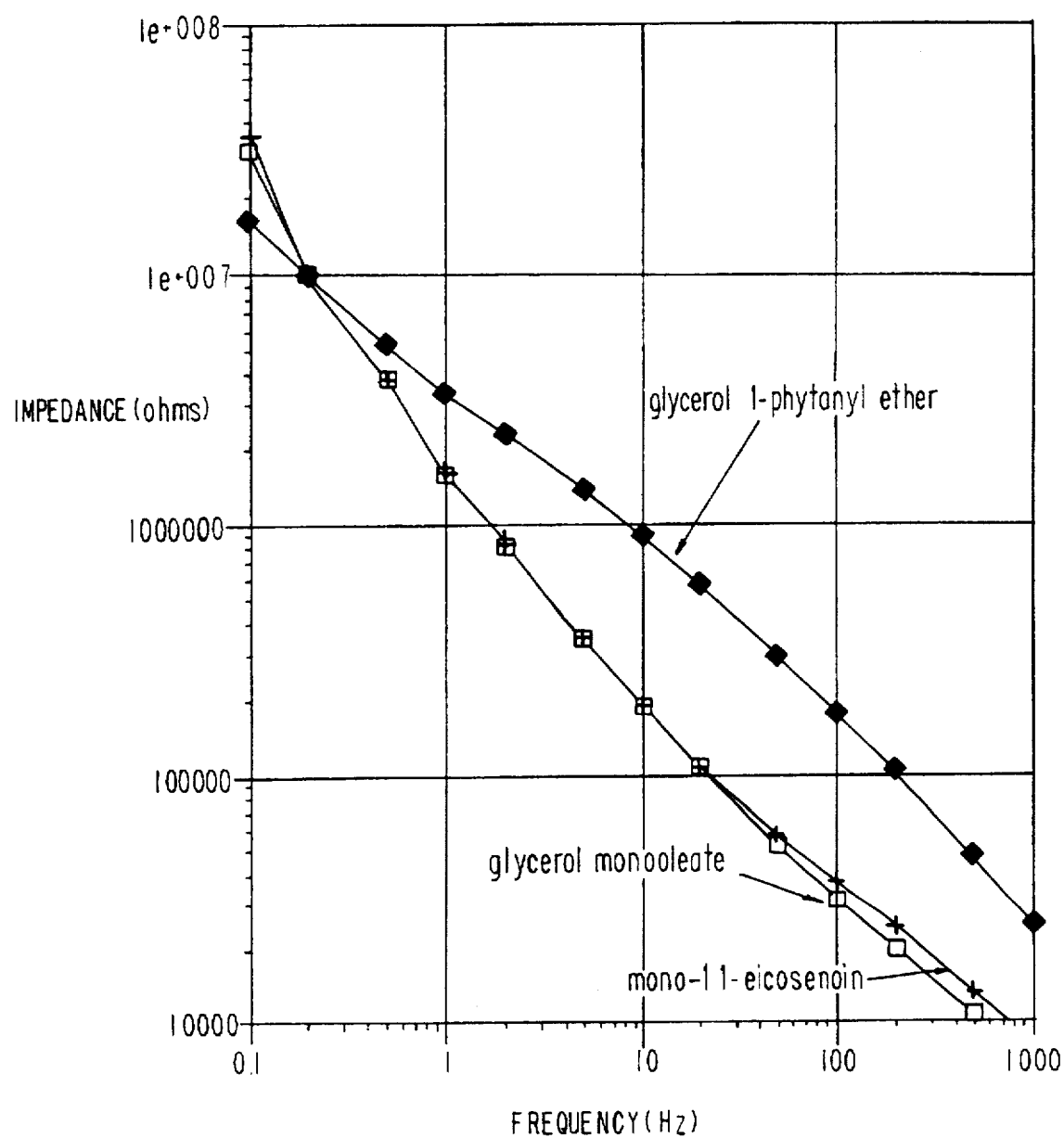
FIG. 6 is a graph of the impedance spectra comparing sealed and unsealed membranes.

A freshly prepared evaporated 2 mm$^2$ gold on glass electrode was immersed in a solution of linker (A) and bis(2-hydroxyethyl)disulfide (HEDS) at a ratio of 8:2 (final concentration was 0.2 mM in ethanol), within five minutes of preparation. After allowing the disulfide species to adsorb for a period of between 30 minutes to 3 days the electrodes were rinsed with ethanol, dried and clamped in a containment vessel. Two microlitres of an ethanol solution of glycerol monooleate (GMO) (140 mM) or mono-11-eicosenoin (140 mM) or glycerol 1-phytanyl ether (140 mM) was added to the electrode. These solutions contained no alkane co-solvent. The electrode was then rinsed twice with 0.5 ml of 0.1M saline solution and impedance spectra were obtained and are shown in FIG. 6. It was found that the glycerol 1-phytanyl ether formed useable sealed bilayer membranes whereas both the GMO and the mono-11-ecosenoin did not form sealed membranes.

EXAMPLE 4

Synthesis and Formation of Bilayer Membranes using a Reservoir Phytanyl Lipid

Figure 7:
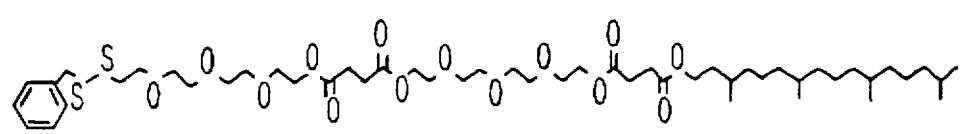
FIG. 7 is a structural diagram for reservoir phytanyl lipid.
Figure 8:
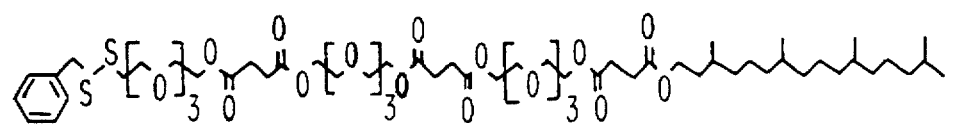
FIG. 8 is a structural diagram for a homologue of the reservoir phytanyl lipid of FIG. 7.

Reservoir phytanyl lipid (B) is shown in FIG. 7. This compound was synthesised from 4,18,21-trioxo-36-phenyl-34,35-dithio-5,8,11,14,17,22,25,28,31-nonaoxohexatricontanoic acid and phytanol in the presence of dicyclohexylcarbodiimide and dimethylamino pyridine. The homologous reservoir phytanyl lipid (C) shown in FIG. 8 was synthesised in analogous fashion from the suitable hydrophilic precursor and phytanol.

A bilayer membrane was formed onto a freshly evaporated gold electrode using the protocol described in Example 2 but in the absence of any small spacer molecule. Thus a solution of reservoir phytanyl lipid (B) or (C) in ethanol was contacted with the gold electrode surface, followed by rinsing of the electrode.

A bilayer membrane was then formed by addition of 5 microlitres of an ethanol solution containing glycerol 1-phytanyl ether (140 mM) and valinomycin (glycerol 1-phytanyl ether/valinomycin 1500:1) followed by 0.1M sodium chloride solution. Impedance spectra were taken before and after addition of potassium chloride solution and values at 10 Hz are shown in Table 3.

TABLE 3

| Reservoir Phytanyl Lipid | NaCl(0.1M) | KCl(0.1M) log/Z/ at 10Hz |
|---|---|---|
| 1:0 | 7.8 | 7.3 |
| 1:10 | 7.5 | 6.4 |
| 1:100 | 7.0 | 6.1 |
| 0:1 | 6.9 | 6.1 |

EXAMPLE 5

Reduced effect of serum on lipid bilayers by incorporation of lipids containing PEG 2000 head groups A freshly prepared evaporated 2 mm$^2$ gold on glass electrode was immersed in a solution of linker (A) and bis(2-hydroxyethyl)disulfide (HEDS) at an 8:2 ratio (final concentration was 0.2 mM in ethanol), within five 25 minutes of preparation. After allowing the disulfide species to adsorb for a period of between 30 minutes to 3 days the electrodes were rinsed with ethanol, dried and clamped in a containment vessel. Two microlitres of an ethanol solution of glycerol monooleate (GMO) (140 mM), succinic acid phytanol half-ester PEG2000 half-ester (PSP-2000) (1–4 mol% relative to GMO) and gramicidin (GMO/gramicidin ratio 1000:1) with 8% tetradecane (v/v relative to ethanol) was added to the electrode. The electrode was then rinsed twice with 0.5 ml of 0.1M saline solution. After the impedance spectrum was obtained, 2 microlitres of whole plasma was added and the impedance spectrum again measured. The absolute impedance values of 1 Hz are shown in Table 4 for various GMO/PSP-2000 lipid ratios.

TABLE 4

| Ratio GMO/PSP-2000 | NaCl(0.1M) | KCl(0.1M) log/Z/ at 1Hz |
|---|---|---|
| 100:0 | 7.3 | 6.5 |
| 99:1 | 7.1 | 6.7 |
| 98.2 | 7.1 | 7.0 |
| 97:3 | 6.9 | 6.8 |
| 96:4 | 6.9 | 6.4 |
| 95:5 | 7.0 | 6.4 |

As can be seen the effect of plasma on the membranes is most effectively reduced at ratios of 1–3 mol % of the PSP-2000 lipid.

EXAMPLE 6
Formation of a protective hydrogel onto a lipid membrane

A lipid membrane was produced onto a gold electrode using the protocol described in Example 2. Excess saline was removed from the containment vessel and ten microlitres of a solution of agar (0.5–5% w/v) in 0.1M sodium chloride was added to the lipid membrane assembly at 40° C. The membrane assembly was allowed to cool to room temperature whereupon the agar gelled forming a protective membrane over the intact lipid membrane. In the case where the lipid membrane contained valinomycin as the ionophore, addition of a potassium solution caused a decrease in the impedance as expected, although the response times were slower—approximately 15 seconds compared to less than 1 second without the gel membrane. It was also found that addition of whole plasma or serum did not have any effect on the lipid membrane for at least 20 minutes when a 0.3% w/v agar gel was used or 1.5 hours when a 3% w/v agar gel was used.

A hydrogel could be also formed onto a lipid membrane by addition of ten microlitres of a solution of acrylamide (4% w/v) and N'N'-bis-methylene-acrylamide (0.3% w/v) in 0.1M sodium chloride tetramethylethylene diamine (0.01%), followed by addition of two microlitres of a 10% solution of ammonium persulfate in 0.1M sodium chloride solution. The acrylamide gelled giving an intact lipid membrane electrode combination which, when the lipid contained the valinomycin ionophore responded to potassium in the usual manner and which protected the lipid membrane from non-specific effects of serum and plasma for up to one hour.

EXAMPLE 7
Formation of an enzyme/ion selective electrode combination electrode A lipid membrane was formed according to the protocol as described in Example 2 but where the ionophore is nonactin at a GMO/nonactin ratio of 3000:1. To the electrode membrane combination was added two microlitres of a 0.5 mg/ml solution of urease in 0.1M sodium chloride solution, allowing the urease to non-specifically bind to the lipid membrane surface as monitored by impedance spectroscopy, as a control identical electrodes were formed but without the urease addition. After 10 minutes 10 microlitres of a solution of urea (0.1M in 0.1M sodium chloride solution) was added to the urease/ion selective electrode combination and to the control. It was found that on addition of the urea the impedance of the urease/ion selective electrode dropped substantially more (impedance at 1 Hz dropped from log 7.3 ohms to log 7.1 ohms) than that of the control (impedance at 1 Hz dropped from log 7.3 ohms to log 7.25 ohms). It is expected that the urease converts the urea to ammonium which is transported by the nonactin across the lipid membrane. A major advantage of this enzyme/ion selective electrode over conventional enzyme/ion selective electrodes is that it is possible to produce inexpensive, single use sensors with fast response times.

EXAMPLE 8
Method of adsorbing Gramicidin B
1st layer

Onto freshly prepared 2 mm² gold electrodes was deposited 2 µl of a ethanolic solution containing 140 mM glycerol monooleate, 140 µM reservoir lipid A, 14 µM MSLXXB, 1.4 µM Gramicidin B, 100 µl 0.1 µM NaCl was immediately added and the assembly allowed to stand overnight. The saline solution was then removed, the assembly rinsed with ethanol (5×100 µl) and drained.

2nd layer

To the above prepared electrode was added 5 µl of a ethanolic solution of 140 mM glycerol monooleate and 1.4 µM biotin-gramicidin conjugate, 2% (v/v) tetradecane. The assembly was immediately treated with 100 µl 0.1M NaCl. The saline solution is removed and replaced with fresh saline (100 µl) five times.

Figure 9:
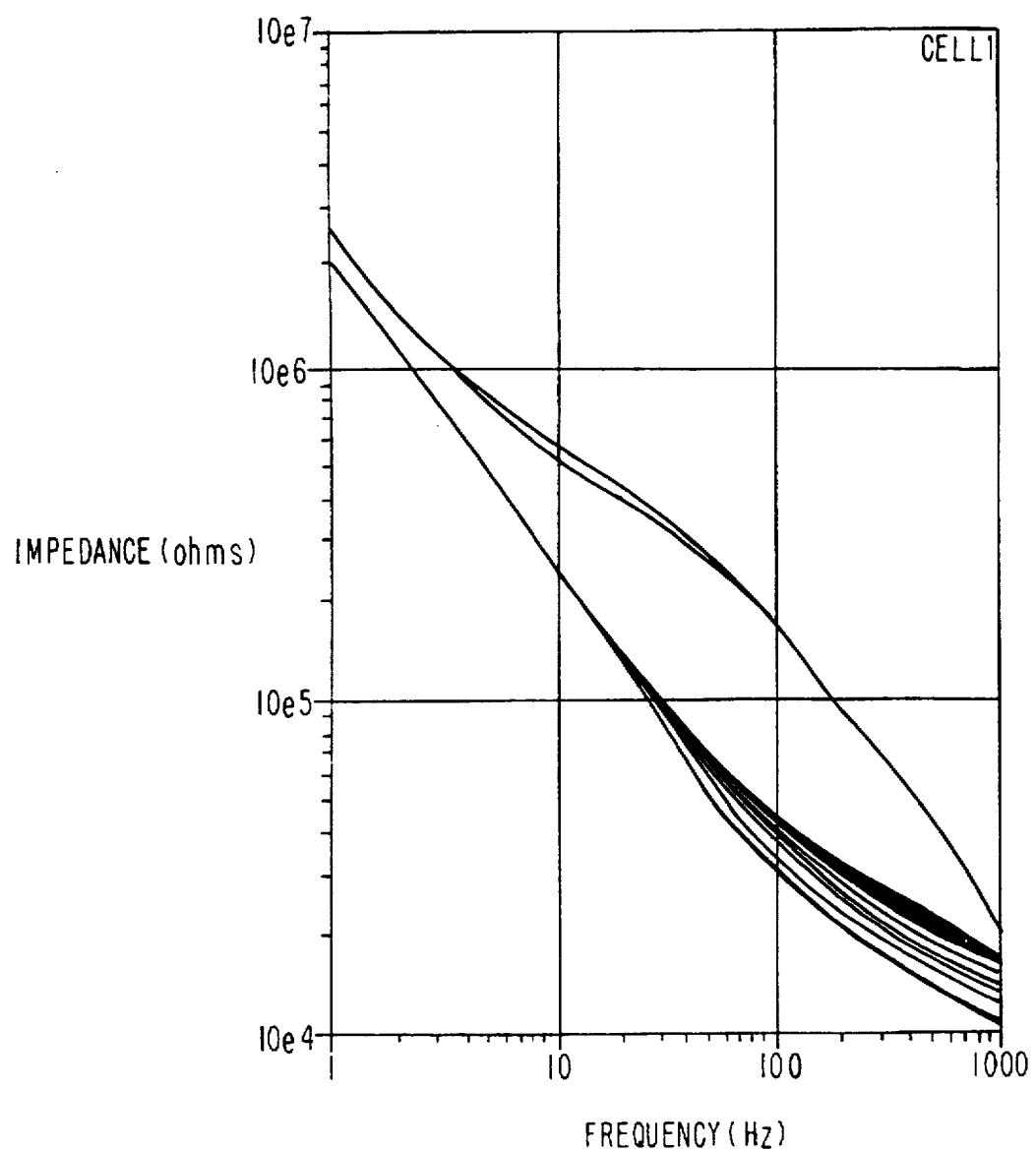
FIG. 9 is a graph of the impedance spectra of electrodes in the presence and absence of streptavidin solution and gramicidin derivative.

FIG. 9 shows the impedance of the electrodes before (a), and after (b) challenge with 1 µl 0.05 mg/ml streptavidin solution (0.1M NaCl). The impedance trace obtained for the sealed membrane, i.e. without gramicidin derivative in the 2nd layer, is shown in (c).

Conducting membranes that respond to the addition of streptavidin can also be obtained by varying the method described above with the following:

1) type of membrane spanning lipid added
2) replacing glycerol monooleate with other different chain length derivatives or glycerol monooleate ether derivatives
3) the concentration of MSLXXB from 1 µM to 140 mM
4) the concentration of Gramicidin B from 1 µM to 14 µM
5) replacing reservoir phytanyl lipid B with reservoir lipid A or reservoir phytanyl lipid C in the concentration range 10 µM to 1 mM.
6) saline can be omitted from the first layer, and glycerol monooleate can also be omitted from the first layer
7) ethanol can be replaced with other polar solvents such as methanol or dioxane
8) the 2nd layer can be made up with or without addition of alkanes such as tetradecane.

EXAMPLE 9
First Layer

Onto a freshly prepared (by evaporation or sputtering) 2 mm² gold electrode is placed 2 ml of a solution comprising glycerolmonooleate (0.14M), reservoir lipid A (1.4 mM) and linker gramicidin B (0.014 mM) in a 98:1 (v/v) mixture of ethanol and tetradecane. The electrode/well assembly is then immediately treated with 100 ml of 0.1M NaCl and the assembly is allowed to stand overnight. The saline solution is then removed and the assembly is washed (5×100 ml ethanol) and drained.

Second Layer

To the above prepared electrode is added a solution of gramicidin-biotin conjugate(0.14 mM) and glyceryl monooleate(0.14M) in ethanol(5 ml). The assembly is then immediately treated with 0.1M saline(100 ml). The saline solution is the removed and replaced with fresh saline(100 ml) five times.

Membranes were formed as described in the above example but with varying concentrations of gramicidin in the two layers. The impedance of the membranes was measured and the membranes challenged with 1 ml 0.5 mg/ml streptavidin. The impedance traces obtained are shown in FIGS. 10–12.

Figure 10:
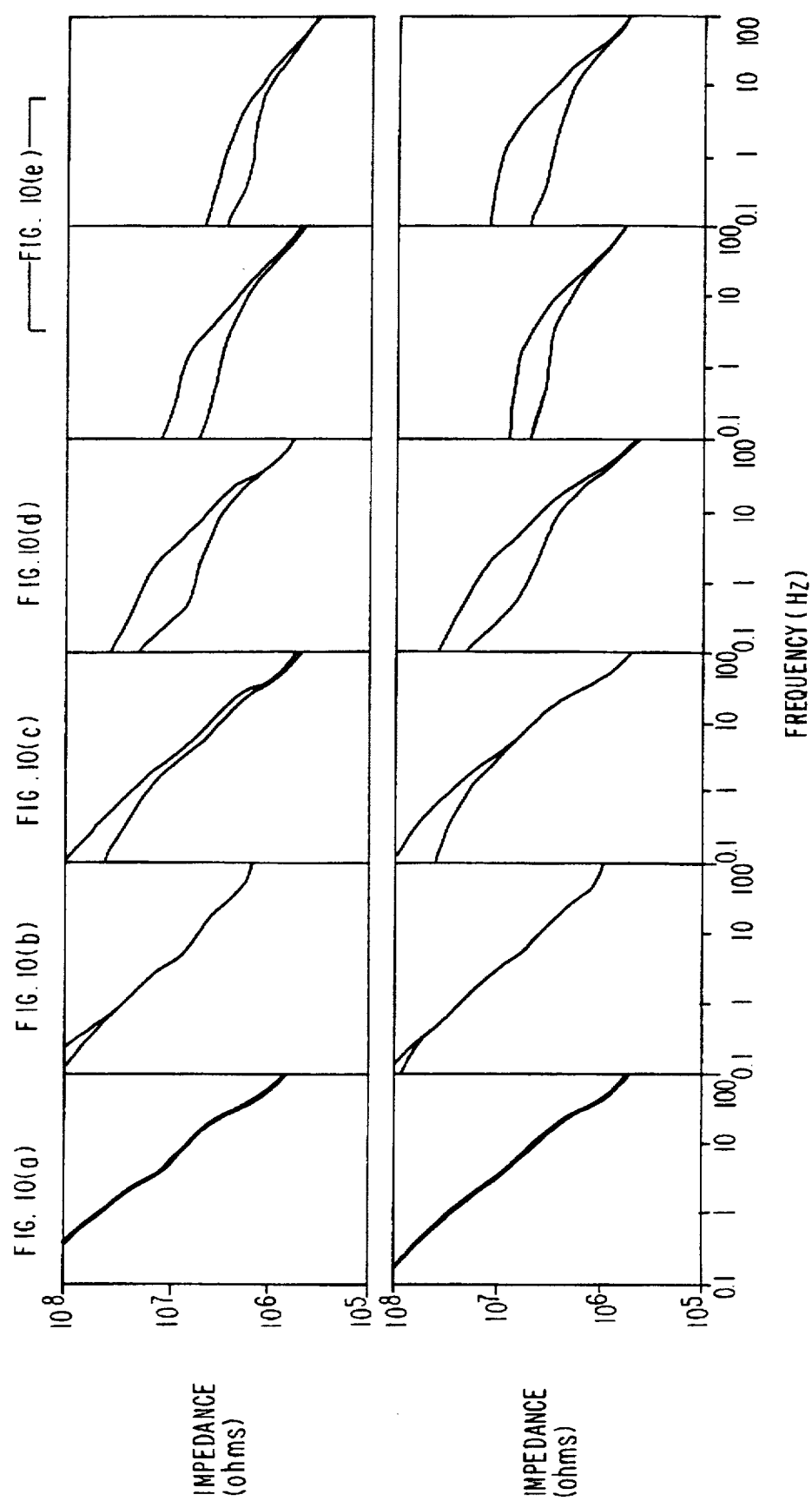
FIG. 10 is a series of traces of impedance spectra for bilayer membranes with varying concentrations of GMO, tetradecane and gramicidin-biotin conjugate conjugate in the layers.

In each of the traces shown in FIGS. 10(a–d) the bottom layer consisted of 0.14 mM double length reservoir gramicidin, 1.4 mM GUDRUN, 140 mM glyceryl monooleate (GMO), 10% tetradecane. The top layers each consisted of GMO, tetradecane (10%) and varying concentrations of gramicidin-biotin conjugate: FIG. 10a-0; FIG. 10b-0.0014 mM; FIG. 10c-0.014 mM; FIG. 10d-0.14 mM.

In FIG. 10e only 0.14 mM gramicidin-biotin cojugate, 140 mM GMO, tetradecane 10% solution was applied to a fresh gold electrode.

Figure 11:
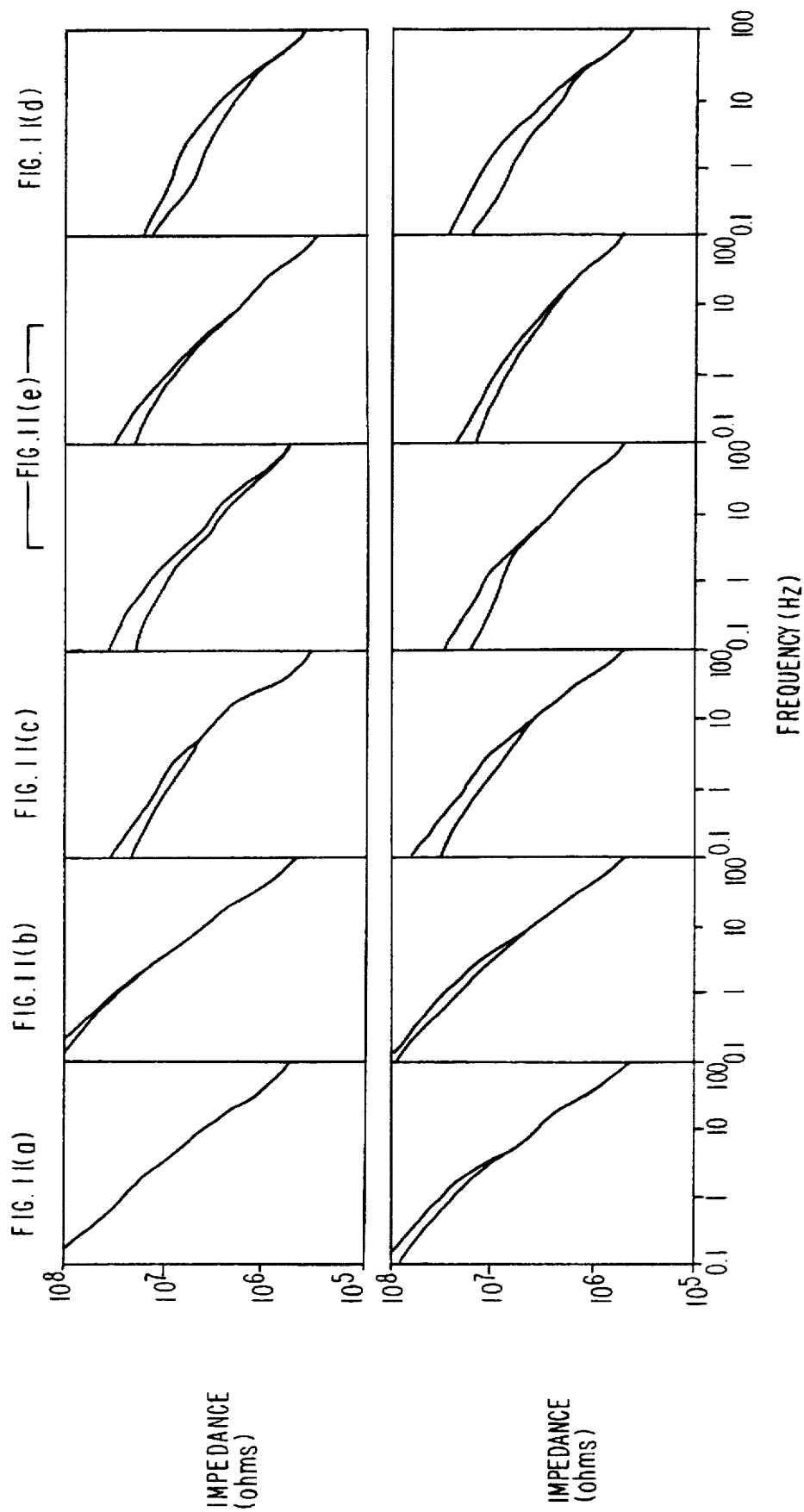
FIG. 11 is a second series of traces of impedance spectra for bilayer membranes with varying concentrations of GMO, tetradecane and gramicidin-biotin conjugate in the layers.
Figure 12:
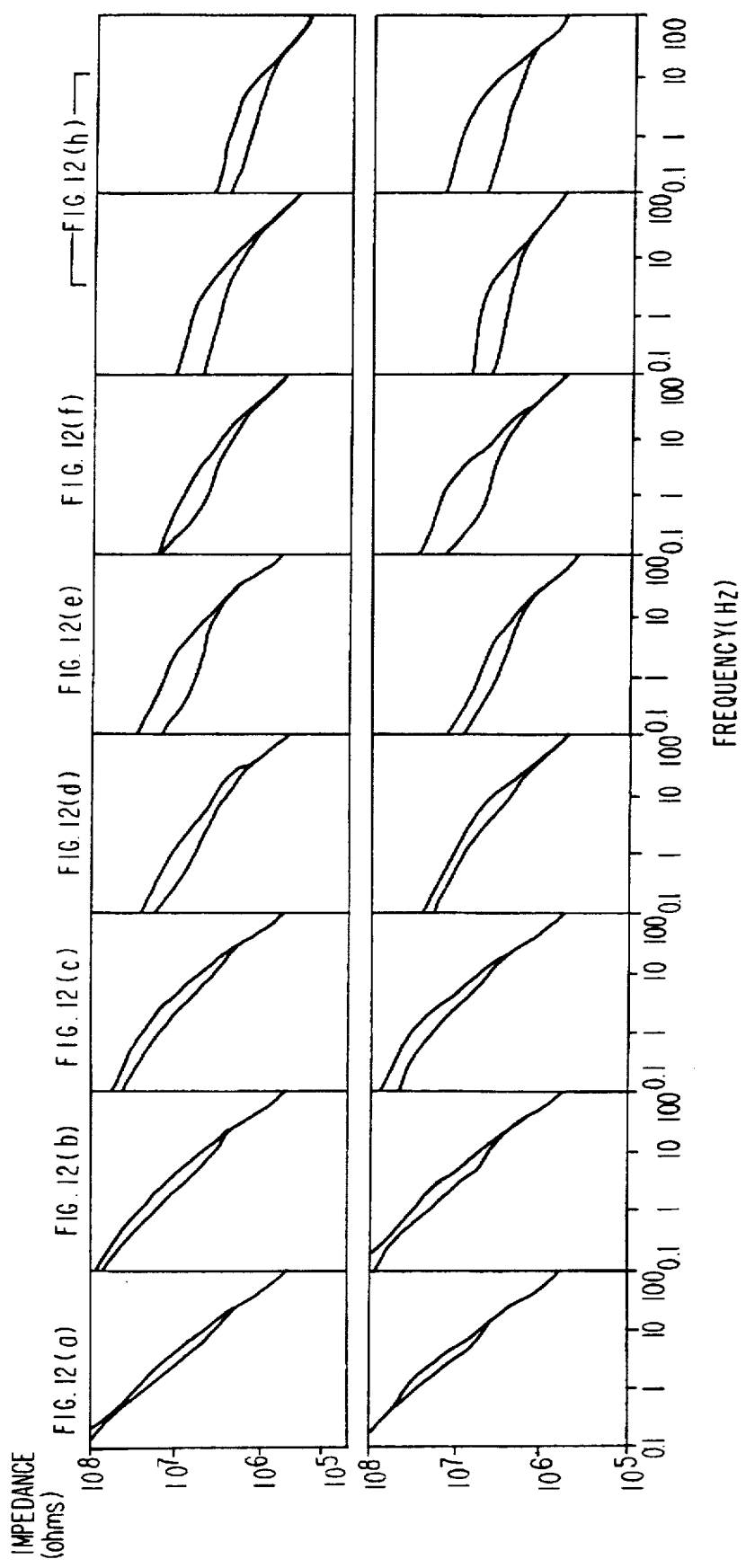
FIG. 12 is a third series of traces of impedance spectra for bilayer membranes in which the concentration of gramicidin in the bottom layer is varied.
Figure 13:
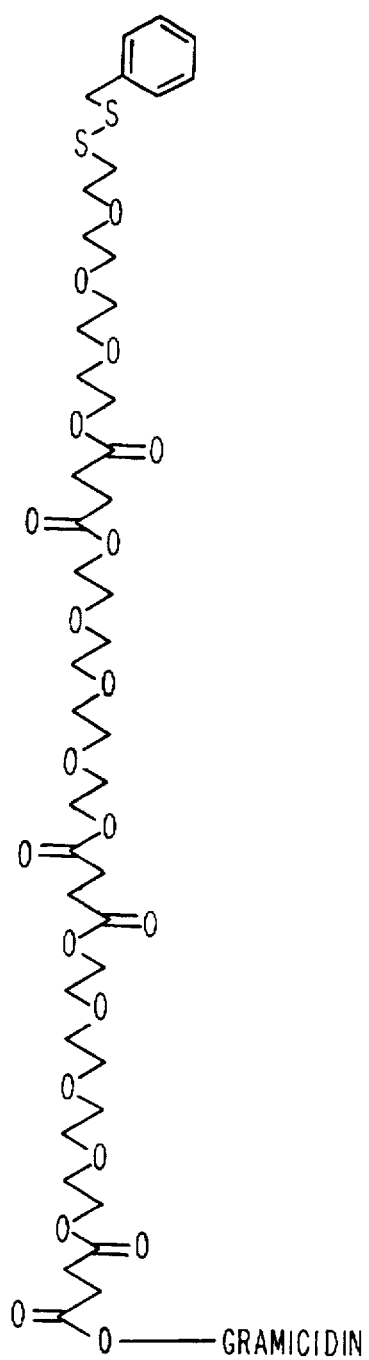
FIG. 13 is a structural diagram for liker gramicidin B, a functionalized gramicidin comprising a gramicidin backbone, a hydrophilic group and a disulfide group.

FIG. 11 is the same as FIG. 10 except that the concentration of double length reservoir gramicidin in the bottom layer for traces a–d was 0.014 mM. In FIG. 11e only 0.014 mM gramicidin-biotin cojugate, 140 mM GMO, tetradecane 10% solution was applied to a fresh gold electrode.

Figure 1:
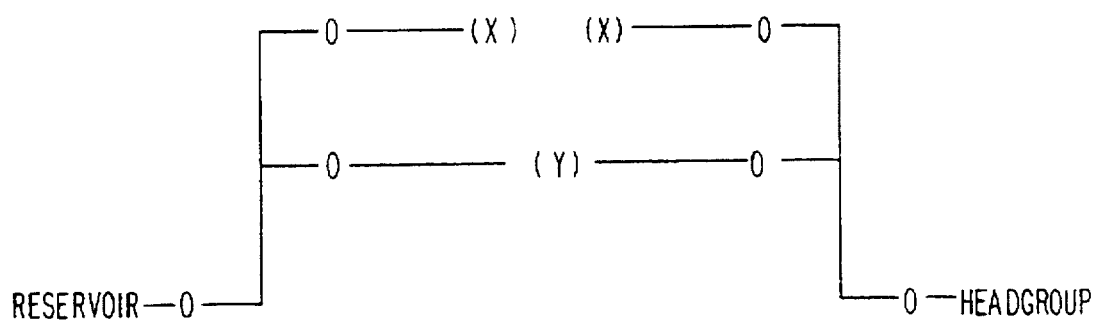
FIG. 1 is a structural diagram of a synthetic lipid for use in a bilayer membrane of the invention.

In FIG. 12 the concentration gramicidin-biotin conjugate in the top layer was maintained constant at 0.14 mM and the concentration of double length reservoir gramicidin in the bottom layer varied. FIG. 12a-1.4 nM; FIG. 12b-14 nM; FIG. 12c-140 nM; FIG. 12d-1.4 mM; FIG. 12e-14 mM; FIG. 12f-140 mM. FIG. 10e is repeated as FIG. 12g for comparison.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A method of producing an electrode membrane combination, the method comprising the following sequential steps:
   (1) Forming a solution comprising ion channels having attached at an end thereof a reservoir region, the reservoir region including a hydrophilic group and an attachment group; and a reservoir lipid, the reservoir lipid comprising a hydrophobic region, a hydrophilic region and an attachment region in a polar carrier solvent;
   (2) Contacting the electrode with the solution from step (1), the composition of the electrode and the attachment groups and the attachment regions being selected such that the attachment groups and the attachment regions chemisorb to the electrode;
   (3) After a period of incubation rinsing the coated electrode from step (2) to remove unbound material;
   (4) Adding to the rinsed electrode from step (3) a solution comprising ion channels and a lipid in a carrier solvent; and
   (5) Adding to the electrode from step (4) an aqueous solution such that a lipid bilayer membrane coating the electrode is formed.

2. A method as claimed in claim 1 in which the solution in step 1 further includes a lipid.

3. A method as claimed in claim 1 in which the ion channels are gramicidin or analogues or derivatives thereof.

4. A method as claimed in claim 1 in which the ion channels are linker gramicidin B.

5. A method as claimed in claim 1 in which the reservoir lipid is 23-(20'-Oxo-19'-oxaeicosa-(Z)-9'-ene)-70-phenyl-20,25,28,42,45-pentaoxo-24-aza-19,29,32,35,38,41,46,47,52,55-dec aoxa-58,59-dithiahexaconta-(Z)-9-ene or reservoir phytanyl lipid (B) or reservoir phytanyl lipid (C).

6. A method as claimed in claim 1 in which the reservoir lipid used in the solution in step 1 has a biotin containing head group.

7. A method as claimed in claim 1 in which the reservoir lipid used in step 1 has a head group used to couple the reservoir lipid to a protein molecule.

8. A method as claimed in claim 1 in which the reservoir lipid used in step 1 has as a head group a polyethylene glycol or phosphatidyl choline group.

9. A method as claimed in claim 1 in which the lipid in the solution in step 1 and/or step 4 is glycerol monoalkenoate.

10. A method as claimed in claim 9 in which the lipid is a glycerol monoalkenoate where the alkenoate group may be an unsaturated hydrocarbon chain of between 16–22 carbons in length.

11. A method as claimed in claim 1 in which the lipid in the solution in step 1 and/or step 4 is glycerol monooleate.

12. A method as claimed in claim 1 in which the lipid in step 4 is a glycerol monoalkyl ether where the alkyl group is a hydrocarbon chain of between 16–22 carbons in length.

13. A method as claimed in claim 1 in which the lipid in step 4 is glycerol monooleate, glycerol monopalmitoleic, mono-11-eicosenoin, or mono-erucin.

14. A method as claimed in claim 1 in which the lipid in step 4 is glycerol monophytanyl ether.

15. A method as claimed in claim 1 in which the lipid in step 4 is a mixture of glycerol monoalkyl ether or glycerol monoalkenoate and a lipid where the head group is a polyethylene glycol group of between 600–6000 g/mol.

16. A method as claimed in claim 1 in which the lipid in step 4 is a mixture of glycerol monoalkyl ether or glycerol monoalkenoate and 1–3% of a lipid where the head group is a polyethylene glycol group.

17. A method as claimed in claim 16 in which the polyethylene glycol has a molecular weight in the range of 600–3000 g/mol.

18. A method as claimed in claim 16 in which the polyethylene glycol containing lipid comprises in the same molecule a phytanyl group attached to a succinate group at one end and a polyethylene glycol 2000 attached to the other end of the succinate.

19. A method as claimed in claim 1 in which the lipid in step 4 is a mixture of glycerol monoalkyl ether or glycerol monoalkenoate and a lipid where the head group is a phosphatidyl choline head group.

20. A method as claimed in claim 1 in which the lipid in step 4 is a mixture of glycerol monoalkyl ether or glycerol monoalkenoate and up to 20% of a lipid where the head group is a phosphatidyl choline head group.

21. A method as claimed in claim 1 in which the lipid in step 4 is a mixture of glycerol monoalkyl ether or glycerol monoalkenoate and up to 20% of a lipid where the head group is a phosphatidyl choline head group and up to 3% of a lipid where the head group is a polyethylene glycol of molecular weight between 600–3000 g/mol.

22. A method as claimed in claim 1 in which the lipid in step 4 is a mixture of glycerol monoalkyl ether or monoalkenoate and a lipid where the head group is a Galβ1-3-GalNAcβ1-4Gal(3-2α-NeuAc)β1-4Glc-1-1 ceramide carbohydrate head group.

23. A method as claimed in claim 1 in which the solutions in steps (1) and (4) contain less than 2% decane, dodecane, tertradecane or hexadecane.

24. A method as claimed in claim 1 in which the solutions in steps (1) and (4) contain no decane, dodecane, tetradecane or hexadecane.

* * * * *